United States Patent
Shulman et al.

(10) Patent No.: US 9,814,252 B2
(45) Date of Patent: Nov. 14, 2017

(54) POLAR LIPID MIXTURES, THEIR PREPARATION AND USES

(75) Inventors: Avidor Shulman, Kiryat Tivon (IL); Rassan Zuabi, Kfar Neen (IL); Gai Ben Dror, Moshav Ofer (IL); Yoni Twito, Geva Carmel (IL); Dori Pelled, Hod Hasharon (IL); Yael Herzog, Nesher (IL)

(73) Assignee: ENZYMOTEC LTD., Migdal Haemeq (IL)

( * ) Notice: Subject to any disclaimer, the term of this patent is extended or adjusted under 35 U.S.C. 154(b) by 225 days.

(21) Appl. No.: 13/205,071

(22) Filed: Aug. 8, 2011

(65) Prior Publication Data

US 2011/0294757 A1    Dec. 1, 2011

Related U.S. Application Data

(63) Continuation of application No. 11/912,925, filed as application No. PCT/IL2006/000510 on Apr. 27, 2006, now abandoned.

(30) Foreign Application Priority Data

Apr. 28, 2005 (IL) .......................... 168294

(51) Int. Cl.
   *A23J 7/00*       (2006.01)
   *A23L 33/115*     (2016.01)

(52) U.S. Cl.
   CPC ............... *A23J 7/00* (2013.01); *A23L 33/115* (2016.08); *A23V 2002/00* (2013.01)

(58) Field of Classification Search
   None
   See application file for complete search history.

(56) References Cited

U.S. PATENT DOCUMENTS

| | | | |
|---|---|---|---|
| 5,677,472 | A | 10/1997 | Nyberg et al. |
| 5,709,888 | A | 1/1998 | Gil et al. |
| 6,036,932 | A | 3/2000 | Borror et al. |
| 6,949,528 | B1 | 9/2005 | Goddard et al. |
| 2004/0022922 | A1 | 2/2004 | Rutenberg |

FOREIGN PATENT DOCUMENTS

| | | |
|---|---|---|
| EP | 0484266 A2 | 5/2002 |
| JP | 62179351 | 8/1987 |
| JP | 3047192 | 2/1991 |
| JP | 7173182 | 7/1995 |
| WO | 03105609 A1 | 12/2003 |
| WO | 2005051091 A1 | 6/2005 |

OTHER PUBLICATIONS

Human Physiology, Human Milk—The perfect food for Human Babies, (Jan. 16, 20014), p. 1.*
A. Sala Vila, High-performance liquid chromatography with evaporative light-scattering detection for the determination of phospholipid classes in human milk, infant formulas and phospholipid sources of long-chain polyunsaturated fatty acids, Journal of Chromatography A., 2003, pp. 73-80, vol. 1008.
Kuban State Technology University , "Improving the Technology for Obtaining Skim Phospholipids", pp. 1-3, 2001, InformCrossScience (Translation of Russian article attached).
Joel Bitman PhD et al., Comparison of the lipid composition of breast milk from mothers of term and preterm infants, Am. J. Clin. Nutr., 1983, pp. 300-312, vol. 38.
Joel Bitman PhD et al., Comparison of the phospholipid composition of breast milk from mothers of term and preterm infants during lactation, Am. J. Clin. Nutr., 1984, pp. 1103-1119, vol. 40.
Max Ruegg et al., The fat globule size distribution in human milk, Biochim. Biophys. Acta, 1981, pp. 7-14, vol. 666.
Betty Ann Brody PhD et al., Sequence of Central Nervous System Myelination in Human Infancy. I. An Autopsy Study of Myelination, J. Neuropathol. Exp. Neurol., 1987, pp. 283-301, vol. 46.
Hanna C. Kinney M.D. et al., Sequence of Central Nervous System Myelination in Human Infancy, J. Neuropathol. Exp. Neurol., 1988, pp. 217-234, vol. 47.
Chiara Luberto et al., Sphingolipid Metabolism in the Regulation of Bioactive Molecules, Lipids, 1999, pp. S5-S11, vol. 34 (suppl).
Kyoichi Oshida et al., Effects of Dietary Sphingomyelin on Central Nervous System Myelination in Developing Rats, Pediatric Research, 2003, pp. 589-593, vol. 53.
R. Rombaut et al., Analysis of Phospho- and Sphingolipids in Dairy Products by a New HPLC Method, J. Dairy Sci., 2005, p. 482-488, vol. 88.
International Search Report for PCT/IL2006/000510 published May 31, 2007 filed Apr. 27, 2006 (U.S. Appl. No. 11/912,925 claims priority to this PCT).
International Preliminary Report on Patentability for PCT/IL2006/000510 published Oct. 28, 2007 filed Apr. 27, 2006 (U.S. Appl. No. 11/912,925 claims priority to this PCT).
Written Opinion of the International Searching Authority for PCT/IL2006/000510 published Oct. 28, 2007 filed Apr. 27, 2006 (U.S. Appl. No. 11/912,925 claims priority to this PCT).
Jensen, R.G. et al, Lipids, vol. 15, No. 5, 1980, pp. 345-355.
Bitman et al. "Comparison of the phospholipid composition of breast milk from mothers of term and preterm infants during lactation" Am J Clin Nutr 40(5): 1103-19 (1984).
Hamosh et al. "Lipid composition of preterm human milk and its digestion by the infant" Composition and Physiological properties of Human Milk: 153-64 (1985).
Hamosh et al. "Lipids in milk and the first steps in their digestion" Pediatrics 75(1 Pt 2): 146-50 (1985).

(Continued)

*Primary Examiner* — Dennis J Parad
*Assistant Examiner* — Lyndsey Beckhardt
(74) *Attorney, Agent, or Firm* — John P. White; Cooper & Dunham LLP

(57) ABSTRACT

Disclosed herein are polar lipid mixtures, comprising glycerophospholipids such as phosphatidylcholine (PC), phosphatidylethanolamine (PE), phosphatidylserine (PS) and phosphatidyl-inositol (PI), and sphingolipids such as sphyngomyelin (SM). Most importantly, the ratio of phospholipids in said mixture is comparable to that of HMF, and is represented by SM>PC>PE>PS>PI or SM=PC>PE>PS>PI. Processes for the preparation of said mixtures and uses thereof are also described herein.

1 Claim, No Drawings

(56) References Cited

OTHER PUBLICATIONS

Harzer et al. "Changing patterns of human milk lipids in the course of the lactation and during the day" Am J Clin Nutr 37(4): 612-21 (1983).
Bitman and Wood. "Changes in Milk Fat Phospholipids During Lactation" J Dairy Sci 73: 1208-1216 (1990).
Jensen et al. "Composition of the lipids in human milk: a review" Lipids 15(5) : 345-55 (1980).
Jensen et al. "Lipids of bovine and human milks: a comparison" J Dairy Sci 73(2): 223-40 (1990).
Kivinen et al. "Milk and egg phospholipids act as protective surfactants against lumind acid in Necturus gastric mucosa." Aliment Pharmacol Ther 9: 685-691 (1995).
Wang et al. "Comparison of the fatty acid composition of total lipids and phospholipids in breast milk from Japanese women" Pediatr Int 42(1): 14-20 (2000).

* cited by examiner

POLAR LIPID MIXTURES, THEIR PREPARATION AND USES

CROSS REFERENCE TO RELATED APPLICATIONS

This application is a Continuation application of U.S. patent application Ser. No. 11/912,925, filed May 12, 2008, which is a U.S. National Stage Application of International Application No. PCT/IL06/00510, filed Apr. 27, 2006, which claimed priority to Israeli Application No. 168294, filed Apr. 28, 2005. The entire content of each of these identified applications is incorporated herein by reference.

FIELD OF THE INVENTION

The present invention relates to polar lipids preparations, in particular mixtures comprising glycerophospholipids, optionally with sphingomyelin, their preparation and uses.

BACKGROUND OF THE INVENTION

All publications mentioned throughout this application are fully incorporated herein by reference, including all references cited therein.

Human milk fat (HMF) is composed of about 30-40 g/L lipids. Of those, approximately 98% are triglycerides, 0.3-1% phospholipids, and 0.4% cholesterol. The phospholipids are composed of four major moieties: sphingomyelin (SM), phosphatidylcholine (PC), phosphatidylethanolamine (PE), phosphatidylserine (PS), and phosphatidylinositol (PI).

Although glycerophospholipids, sphingomyelin, cholesterol and their derivatives are found in relatively small amounts in mother's milk, they play an important role in the nutrition of developing infants, and have essential roles in all physiological systems and cycles of the human body.

Total fat content increases gradually from colostrum (2.0%) through transitional (2.5% to 3.0%) to mature milk (3.5% to 4.5%) [Bitman et al. (1983) *Am. J. Clin. Nutr.* 38:300-312].

The role of phospholipids, and especially the role of the phospholipid backbone, in human breast milk is poorly understood. Most scientific research on human breast milk phospholipids in fact uses them as an assay for the intake and incorporation of different fatty acids on the phospholipid skeleton.

Phospholipids are involved in the structure of human milk fat globules membrane (HMFGM), representing 23% of the membrane mass. Interestingly, in contrast to the significant changes in fatty acid composition from woman to woman, related mainly to race and diet, the phospholipid composition remains constant, and is not influenced by diet. Essentially, the level of phospholipids in human breast milk only changes with the age of the infant. This further suggests that phospholipids are an essential nutritional component of human breast milk.

Phospholipids show a decrease from high levels in colostrum (1.1% out of the total fat fraction) to lower levels in mature milk (0.6%). The decline in phospholipids is consistent with an increase in the fat globule size [Ruegg et al. (1981) *Biochim. Biophys. Acta* 666, 7-14]. The phospholipids composition of breast milk from mothers of term and preterm infants during lactation was thoroughly studied by Bitman et al. [Bitman et al. (1984) *Am. J. Clin. Nutr.* 40, 1103-1119].

Milk phospholipids do not exhibit any marked differences attributable to length of gestation after day 21. This remarkable constancy in class distribution of phospholipids indicates that the composition of the membrane of the milk fat globules is identical at all stages of lactation.

The amount of phospholipids (sphingomyelin and glycerophospholipids) in human milk fat is about 15-20 mg/dL. Sphingomyelin (SM) is found at about 37% of total polar lipids, phosphatidylcholine (PC) is found at 28% of total polar lipids, phosphatidyl-ethanolamine (PE) is found to be about 19%, phosphatidylserine (PS) at 9% and phosphatidylinositol (PI) at 6%. Thus, the ratio between the polar lipids of HMF is as follows: SM>PC>PE>PS>PI.

Some glycerophospholipids, and especially those extracted from soybean, are used as dietary supplements and a variety of health benefits are associated with their intake, including improvement of cognitive functions, as well as of memory and concentration, maintenance of cellular membrane composition, and contribution to general well-being. Phospholipids and lecithins are a source of choline and they enhance the bio-availability of other nutrients and therapeutic agents.

In addition, glycerophospholipids are used as food emulsifiers, anti-oxidants, stabilizers, as well as in other food application such as mold-release and anti-caking agents. They confer unique physical properties to food products as well as personal care products, and thus are also used in pharmaceutical formulations as carriers and delivery systems.

WO 03/105609 describes a phospholipid supplement which contains PS at a concentration of at least 1% out of the total phospholipid content of the composition. Moreover, said PS is derived from soybean lecithin, rapeseed lecithin or egg yolk, and is enzymatically produced using phospholipase-D.

U.S. Pat. No. 5,709,888 presents fat mixtures comprising phospholipids and LC-PUFA, such as oleic acid, linoleic acid and alpha-linolenic acid, having an adequate level of LC-PUFA of both the n6 and n3 series.

EP 484,266 describes a mixture of phospholipids obtained from domestic animal brain sources, in addition to at least one of vegetable oil, animal fat, fish oil, and/or medium chain triglycerides, in which the ratios between LC-PUFA and phospholipids is similar to those of human milk and mediterranean diet.

Most of the sphingomyelin in milk fat is a building block of the milk fat globule membrane. Sphingomyelin is also an important building block required by the infant for the development of the brain and other tissues, as well as being important in several biochemical pathways.

Myelin is the white matter coating nerve cells, enabling them to conduct impulses between the brain and other parts of the body. It consists of a layer of proteins, packed between two layers of lipids. Myelin is produced by specialized cells: oligodendrocytes in the central nervous system, and Schwann cells in the peripheral nervous system. Myelin sheaths wrap themselves around axons, the threadlike extensions of neurons that make up nerve fibers. Each oligodendrocyte can myelinate several axons. Myelin is comprised of 80 percent lipids and 20 percent proteins. A major lipid of this important tissue is sphingomyelin. This fatty substance protects the fiber-like axons and speeds electrical signals as they travel along nerve pathways to carry out vital functions such as movement.

Different diseases and syndromes are related to disorders in myelin damage. Multiple sclerosis, for example, causes myelin to disintegrate, causing an obstruction of signal flow, which progressively leads to the loss of motor coordination and other functions.

The development of myelin sheaths and neuronal network in infants is thus crucial and depends on the availability of appropriate lipid building blocks, either from self biosynthesis or from dietary sources, i.e. human breast milk.

Sphingomyelin (SM) is composed of phosphocholine as the polar head group and sphingosine as the backbone of the molecule, and it is therefore classified as a sphingolipid. These molecules are involved in the regulation of cell growth, cell differentiation, and various other functions, including cell-substratum interactions and intracellular signal transduction. Although many foods contain a small amount of SM, its nutritional and physiologic roles have not been fully examined.

The myelin of the Central Nervous System (CNS myelin) has a higher lipid content (65-80%) than that of general cell membranes. SM and sphingolipid metabolites, such as cerebrosides and sulfatides, are prominent components of the myelin sheath. This sheath acts as an insulator for nerve impulses and controls the salutatory mode of conduction via the nodes of Ranvier. Myelination of the human CNS begins from 12 to 14 wk of gestation in the spinal cord and continues into the third decade of life in the intracortical fibers of the cerebral cortex, but the most rapid and dramatic changes occur between midgestation and the end of the second postnatal year [Brody B A et al. (1987) *J. Neuropathol. Exp. Neurol.* 46: 283-301; Kinney H C et al. (1988) *J. Neuropathol. Exp. Neurol.* 47: 217-234]. Myelination accounts for a large part of the more than tripling of brain weight that occurs during this period.

A metabolic pathway for sphingolipids has been reported [Luberto C. and Hannun Y A (1999) *Lipids* 34 (suppl): S5-S11]. SPT (EC 2.3.1.50) is the first step and the rate-limiting enzyme in sphingolipid biosynthesis, catalyzing the synthesis of 3-ketosphinganine from L-serine and palmitoyl-CoA. This enzyme is located in the endoplasmic reticulum or Golgi apparatus. A recent study showed that SPT activity gradually increases from the third prenatal to the third postnatal week in the hypothalamus of rats. As myelination begins at the same period in these animals, it is conceivable that an increment of SPT activity may be one of the major factors involved in myelinogenesis.

CNS myelin has a high cerebroside content when compared to its level in other tissues. Cerebroside is generated from ceramide by ceramide UDP-galactosyltransferase, which is the key enzyme in the biosynthesis of cerebrosides and catalyzes the transfer of galactose from UDP-galactose to ceramide. In rats, cerebroside is hardly detectable in the brain before 10 d after birth, but the cerebroside content increases markedly from the second to the third postnatal weeks, especially between day 14 and 23 of life. Because the period of maximum cerebroside biosynthesis corresponds with the time of most active myelination, cerebroside is generally recognized as a universal marker of CNS myelination.

Ceramides can be generated from L-serine and palmitoyl-CoA through de novo synthesis by the enzyme SPT, and from SM by sphingomyelinase. Therefore, it was hypothesized by Oshida et al. (*Pediatric Research* 2003, 53:589-593) that during the period of low SPT activity, cerebroside in CNS myelin of developing rats may be mainly derived from dietary SM ingested in milk that is transformed to ceramide and then to cerebroside. Oshida et al. have shown that when the activity of SPT was inhibited through the administration of an appropriate inhibitor, causing a decrease of cerebrosides in rat CNS myelin, the normal maturation and weight of the myelin tissue could be maintained through the administration of dietary SM. Dietary supplementation of SM restored the brain weight and myelin dry weight that were decreased by the SPT inhibitory treatment. Furthermore, electron microscopy showed that the axon diameter of the inhibited group was restored following the introduction of dietary SM. These findings suggest that orally ingested SM is transformed to ceramide or other metabolites in the intestinal tract, which are absorbed from the bowel and entered the circulation to reach the CNS across the blood-brain barrier.

Although sphingomyelin has been thought to be an inert constituent of cell membranes, current studies suggest that metabolites of sphingomyelin are involved in signal transduction pathways. SM plays a key role in the regulation of cellular processes. Dietary SM can contribute to myelination of developing CNS and protect against toxic and inhibitory conditions. SM is also a building block to other lipids, such as ceramides.

Breast-feeding seems to contribute to rapid growth of brain weight, which is mostly the result of myelination. At birth there is very little myelin, but by 3 years, most axons have myelin coatings.

Since the human milk fat globule membrane resembles the structure and/or function of cell membranes, it is curious that its level of SM is so high, suggesting that the presence of SM can be attributed not just to its role of membrane building block, but also as a dietary source for SM. This role is of great importance at early stages of gestation in order to provide SM for myelin build-up prior to the completion of the biosynthetic route of cerebrosides, as described above. Indeed, the higher levels of phospholipids in general, and of SM in particular, at the early stages of gestation may not be coincidental but rather required to supply dietary SM to compensate the just developing biosynthetic machinery of cerebrosides.

Sphingomyelin is usually not produced on commercial levels, and it is produced only from animal sources, such as bovine milk, eggs, or animal brain. Animal sources, especially those related to brain tissues, are of course avoided in infant nutrients due to the risk of prion disease. In most cases, sphingomyelin of animal sources is produced at high levels of purity, mainly for purposes of analytical standards and for scientific research. These high purity sphingomyelin preparations are characterized by their extremely high cost and scarce availability, and thus are also not feasible for general popular consumption.

Recently, the dairy industry has started to utilize dairy waste to produce nutritional preparations which contain milk proteins, carbohydrates and small amounts of lipids. The latter include neutral lipids as well as polar lipids, including glycerophospholipids as well as sphingolipids, among them sphingomyelin. These preparations contain extremely low levels of sphingomyelin and phosphatidylserine, making them incompatible as an industrial source for these nutrients. A typical preparation (e.g. SM3 Powder, produced by S.A. Corman of Belgium), contains about 4% w/w of PC, 3.2% w/w of PE, 1.6% w/w of PS, 0.9% w/w of PI and about 2.6% w/w of SM. Such low levels would entail use of very large quantities of such preparations in order to deliver even small amount of PS and sphingomyelin. Furthermore, such large quantities would result in the delivery of non-required and non-desired proteins and carbohydrates, the latter mainly in the form of lactose.

The above described commercial milk lipids preparations, although having some similarity to HMF polar lipids, still differ from the latter. The ratio between the polar lipids in the above commercial milk-derived preparations is PC>PE>SM>PS>PI, while in HMF, the ratio between the polar lipids is SM>PC>PE>PS>PI. Particularly, in HMF the level of sphingomyelin is always higher than that of PC, the ratio being of about 1.3, while in the above commercial milk-derived preparations, this ratio is about 0.65.

Rombaut and colleagues provide phospholipid compositions of several dairy products [Rombaut et al. (2005) *J. Dairy Sci.* 482:488]. None of the tested dairy products gave a polar lipids ratio that is corresponding to the SM>PC>PE>PS>PI ratio of found in HMF.

As can be seen in Table 1, the lipid composition of a typical commercial milk-derived preparation differs from HMF mainly in the level of sphingomyelin, which is lower than the level of PC, and in the higher level of PE.

TABLE 1

| Lipid class | Commercial milk lipids (% from total polar lipids) | HMF lipids (% from total polar lipids) |
|---|---|---|
| SM | 21.1 | 37.5 |
| PC | 32.5 | 28 |
| PE | 26.0 | 19.5 |
| PS | 13.0 | 9 |
| PI | 7.4 | 6 |
| Total | 100 | 100 |

In WO 2005/051091, the present inventors described a composition that mimics the phospholipid composition of human breast milk. The present invention concerns the polar lipids of human breast milk and the importance of their supplementation by other sources in infant as well as in adult nutrition. Thus, it is an aim of the present invention to provide lipid preparations, particularly cost effective preparations, with high levels of cerebral-like lipids for advanced infant nutrition and for use in dietary supplements, functional foods and pharmaceutical compositions for promoting brain health.

WO 2005/051091 describes lipid preparations mimicking the polar lipid composition of human breast milk fat (HMF), which includes glycerophospholipids such as PC, PE, PS, and PI as well as other polar lipids, such as sphingomyelin. These lipid preparations are essentially obtained from mixtures of vegetable-derived phospholipids, preferably soybean, as well as structured phospholipids, such as trans-phosphatidylated lecithins. Other lipid preparations mimicking the polar lipids of HMF described in said publication comprise bovine milk-derived sphingomyelin. In that earlier application, the inventors used pure bovine milk sphingomyelin, obtainable as an analytical standard or research chemical, which is not particularly suitable for use in infant nutrition or dietary supplements due to its high cost and extremely low availability, as mentioned previously.

Thus, it is a purpose of the current invention to provide polar lipid preparations mimicking the polar lipids of HMF, optionally comprising SM, wherein the source of said polar lipids is a natural non-brain lipid source.

It is another object of the present invention to provide a dietary supplement which guarantees the sufficient and recommended intake of phospholipids, especially of PS and sphingomyelin, in the form of a mimetic substitute of the phospholipids from human breast milk lipid, aimed especially for infants and young children consumption, as well as pregnant women. Other uses and objects of the invention will become apparent as the description proceeds.

SUMMARY OF THE INVENTION

The present invention relates to a lipid preparation which comprises a mixture of polar lipids, particularly glycerophospholipids being phosphatidyl-choline (PC), phosphatidylethanolamine (PE), phosphatidylserine (PS) and phosphatidyl-inositol (PI), and optionally or non-optionally comprising sphingolipids or a precursor or metabolite thereof, preferably sphingomyelin, wherein the level of each of said PC, PE, PS and PI is at least 1% w/w, and wherein said polar lipids are derived from a natural non-brain animal lipid source.

The lipid preparation of any one of claims 1 and 2, wherein the quantitative ratio between said glycerophospholipids is substantially equivalent to said ratio in naturally occurring human milk fat (HMF), at any desired stage of lactation.

In one embodiment, the lipid preparation of the invention comprises a sphingolipid or a precursor or a metabolite thereof, preferably sphingomyelin, wherein the quantitative ratio between the glycerophospholipids and the sphingolipid in said preparation is essentially equivalent to their corresponding ratio in said naturally occurring HMF, at any desired stage of lactation.

Thus, the ratio between the polar lipids in the lipid preparation of the invention is PC>PE>PS>PI, or SM>PC>PE>PS>PI, or even SM=PC>PE>PS>PI.

In another embodiment said polar lipids are obtained from said natural non-brain animal lipid source by fractionation and/or extraction, or by a method that does not involve transphosphatidylation.

Advantageously, the polar lipids comprising in said lipid mixture are obtained from said natural non-brain animal lipid source by fractionation and/or extraction, particularly by methods which do not involve transphosphatidylation.

The quantitative ratio between said glycerophospholipids may essentially mimic their corresponding ratio in naturally occurring human milk fat (HMF), at any desired stage of lactation. Likewise, when the preparation contains sphingomyelin (SM) or a precursor or a metabolite thereof, the quantitative ratio between the glycerophospholipids and the sphingomyelin in said preparation may essentially mimic their corresponding ratio in said naturally occurring HMF, at any desired stage of lactation.

In a particular embodiment, the invention relates to a lipid preparation which is rich in PS, containing about 5-99% w/w PS, preferably about 5-90% w/w, more preferably about 7-60% w/w, most preferably about 7-25% w/w, wherein the PS is obtained from a natural non-brain animal lipid source by methods which do not involve transphosphatidylation, and wherein said lipid source is preferably a marine source, milk or eggs, more preferably bovine milk. This preparation may comprise additional polar lipids, preferably PC, more preferably a mixture of PC, PE, PI, most preferably a mixture of PC, PE, PI, and SM. The PS may be characterized by a fatty acid profile characteristic of the animal source from which it is derived, preferably the fatty acid profile of bovine milk PS.

In another particular embodiment, the invention relates to a lipid preparation which is rich in SM, containing about 5-99% w/w SM, preferably about 5-90% w/w, more preferably about 10-60% w/w, most preferably about 10-50% w/w, wherein the SM is derived from a natural non-brain animal lipid source. The SM may be characterized by a fatty acid profile characteristic of said animal source, preferably the fatty acid profile of bovine milk SM.

Still further, the invention relates to a lipid preparation which is rich in both PS and SM, containing about 5-99% w/w PS and SM, preferably about 5-90% w/w, more preferably about 7-60% w/w, most preferably about 7-50% w/w, wherein the PS and SM are derived from a natural non-brain animal lipid source by a method which does not involve transphosphatidylation, said lipid source being preferably milk or eggs, more preferably bovine milk.

In a further aspect, the invention relates to a process for the preparation of a lipid preparation which comprises a mixture of polar lipids, particularly glycerophospholipids being phosphatidyl-choline (PC), phosphatidyl-ethanolamine (PE), phosphatidylserine (PS) and phosphatidyl-inositol (PI), and optionally or not-optionally comprising sphingolipids or a precursor or metabolite thereof, preferably sphingomyelin, from a natural non-brain animal lipid source, comprising isolating said lipid mixture from said natural non-brain animal lipid source by methods which do not involve transphosphatidylation.

A specific process for the preparation of the lipid preparation of the invention, as described herein, comprises the steps of:
  (a) providing a natural non-brain animal lipid source which has a substantially low content of polar lipids;
  (b) removing non-lipid material from said lipid source, dispersing the lipids, preferably with agitation, in a suitable organic solvent or a mixture of organic solvents;
  (c) separating the dissolved lipid fraction obtained in step (b) and removing the organic solvent therefrom to give a lipid fraction;
  (d) de-oiling the lipid fraction obtained in step (c) at least once to remove any non-polar lipids; and
  (e) filtering and drying the polar lipids obtained in step (d).

This process may further optionally comprise a step of treatment of the lipid source with an aqueous medium, either before or after said step (b).

Suitable organic solvents may be mixtures of a polar organic solvent, preferably a primary alcohol, particularly ethanol, and a non-polar solvent, preferably a hydrocarbon, particularly n-hexane. The organic solvent may optionally contain water.

The process of the invention may be carried out at a temperature of 15-100° C., preferably 25-80° C., more preferably 30-60° C.

The natural non-brain animal lipid source comprises at least one lipid source derived preferably from a marine source, more preferably from an animal origin, most preferably from bovine milk fat or from poultry eggs. The lipid source may be a mixture of lipid sources.

The natural lipid source is preferably derived from bovine milk, and may contain up to 5% w/w, preferably 10% w/w, more preferably 25% w/w, even more preferably 35% w/w of total lipids, in addition to other constituents including proteins and carbohydrates, and wherein about 20%, preferably 30%, more preferably 50%, most preferably 70% of said total lipids are polar lipids.

In a specific embodiment the natural lipid source contains about 0.1-10% w/w PC, about 0.1-5% w/w PE, about 0.1-5% w/w PS, about 0.1-5% w/w PI and optionally contains sphingomyelin, preferably at a level of about 0.1-5% w/w. More specifically, the lipid source comprises about 2.6% w/w SM, about 4% w/w PC, about 3.2% w/w PE, about 1.6% w/w PS and about 0.9% w/w PI.

The lipid preparation resulting of any of the processes described herein is characterized by a ratio of polar lipids of PC>PE>PS>PI, or SM>PC>PE>PS>PI or SM=PC>PE>PS>PI.

The present invention further provides a method for the enrichment of SM in the lipid preparation obtained by any one of the processes described herein, said method comprising further subjecting said preparation to a step of any one of alkaline hydrolysis, enzymatic hydrolysis, preparative chromatography or polar lipid extraction.

In another embodiment the invention relates to a dietary supplement or nutrient which comprises a lipid preparation of the invention. The lipid preparation may be comprised in emulsified or dispersed form, preferably in the form of an essentially aqueous emulsion or dispersion or in dry form.

The invention also relates to a method for preparing a dietary supplement of the invention, by admixing a lipid preparation of the invention with at least one of additives, emulsifiers or carriers. This method may further comprises admixing the lipid preparation with an aqueous liquid medium, said dietary supplement essentially being in an aqueous liquid form. The method may further comprise dispersing, preferably dissolving the lipid preparation in an organic medium, preferably an oil conventionally used in infant formulas, particularly an oil which mimics HMF. Still further, the method may comprise spray-drying the liquid dietary supplement, to provide the dietary supplement in powder form.

The lipid mixtures and preparations of the invention and the dietary supplements or nutrients comprising them may be used as an ingredient of a lipid constituent of infant formulas or as an ingredient of infant formulas.

Still further, the lipid mixtures and preparations of the invention and the dietary supplements, nutrients or food articles comprising them may be used in the enhancement of infants and/or children development, particularly cognitive development and/or in the enhancement of vision development.

A specific food article in accordance with the invention is an infant formula, comprising the lipid preparation or mixture or a dietary supplement comprising the same.

The invention also relates to a process for the preparation of PS derived from a natural non-brain animal lipid source, comprising the step of isolating PS from the polar lipid fraction obtained by the process of the invention. The said natural non-brain animal lipid source preferably comprises at least one lipid source derived preferably from a marine source, more preferably from an animal origin, most preferably from bovine fat or from poultry eggs.

The invention further relates to a process for the preparation of SM derived from a natural non-brain animal lipid source, comprising the step of isolating SM from the polar lipid fraction obtained by the process of the invention. The said natural non-brain animal lipid source preferably comprises at least one lipid source derived preferably from a marine source, more preferably from an animal origin, most preferably from bovine milk fat or from poultry eggs.

In a further aspect, the invention relates to the use of the said PS, SM or PS/SM-rich preparations of the invention in the improvement of cognitive functions, particularly memory, concentration, attention and learning capabilities.

Furthermore, the invention relates to use of the said PS, SM or PS/SM-rich preparations of the invention in the treatment of brain-related illnesses or disorders or for improving cognitive functions, e.g. mood-, memory-, stress-, or age-related disorders and diseases such as dementia and Alzheimer's disease, as well as memory loss and problems of concentration and attention and learning capabilities.

In yet a further embodiment, the invention relates to use of the said SM or PS/SM-rich preparations of the invention for treating, preventing or ameliorating myelin-related disorders or diseases, particularly de-myelination related disorders, such as for example MS. These lipid preparations may also be used for supporting and enhancing in a subject, particularly infants and children, the normal or improved development of myelin sheath and other sphingomyelin-related tissues.

DETAILED DESCRIPTION OF THE INVENTION

In a first aspect, the present invention provides a lipid preparation comprising a mixture of polar lipids, particularly glycerophospholipids being phosphatidylcholine (PC), phosphatidylethanolamine (PE), phosphatidylserine (PS) and phosphatidyl-inositol (PI), and optionally comprising a sphingolipid or a precursor or metabolite thereof, particularly sphingomyelin, wherein the level of each of said PC, PE, PS and PI is at least 1% w/w, and wherein said polar lipids are derived from a natural non-brain animal lipid source.

In said preparations, the ratio between polar lipids is: SM>PC>PE>PS>PI or SM=PC>PE>PS>PI. Thus, the ratio between SM and PC is either >1 or 1:1, preferably 1.1, more preferably 1.3. Alternatively, the ratio between SM and PC is 1.5, preferably 2.

The lipid preparation of the invention is obtained by the treatment, processing and fractionation of natural extracted polar lipids mixtures, preferably containing glycerophospholipids, most preferably also containing sphingomyelin. In a preferred embodiment said natural lipids are animal sourced, preferably from milk of farm animals, particularly bovine, and/or from poultry eggs. In a further embodiment the natural lipid mixture may be derived from a vegetal source, preferably containing sphingomyelin or a precursor or metabolite of sphingomyelin.

In a particularly preferred embodiment the lipid preparation of the invention may be prepared from a commercial bovine milk preparation which contains low, and even extremely low levels of the polar lipids (e.g. the mixture described in Table 2) and where the lipids differ in their internal ratio from the SM>PC>PE>PS>PI ratio that is found in HMF (Table 1 above).

TABLE 2

| Lipid class | Commercial milk lipids (weight %) | Commercial milk lipids (% from total polar lipids) |
|---|---|---|
| SM | 2.6 | 21.1 |
| PC | 4 | 32.5 |
| PE | 3.2 | 26.0 |
| PS | 1.6 | 13.0 |
| PI | 0.9 | 7.4 |
| Total | 12.3 | 100.00 |

In accordance with the present invention, the inventors have processed and selectively extracted the polar lipids of the raw bovine milk-derived starting mixture, thereby increasing the levels of the individual lipids, and obtaining a preparation which is suitable for use as a dietary supplement or as an infant nutrition supplement. Importantly, the relative level of sphingomyelin has been increased, up to a level similar or even higher than the level of PC, thus making the lipid preparation of the invention even more similar to HMF polar lipids. Additionally, the level of PE was lowered, again making it comparable to the relative level of PE found in HMF. Table 3 gives an example of a polar lipid preparation of the invention, and details the relative levels of the polar lipids, namely SM, PC, PE, PS, and PI, as compared to HMF lipids. The SM>PC>PE>PS>PI ratio that is found in HMF, was obtained in the lipid preparation of the invention (table 3), even though the raw bovine milk-derived starting mixture has a different ratio (PC>PE>SM>PS>PI).

TABLE 3

| Lipid class | Lipid preparation of invention (% from total SM, PC, PE, PS, PI) | HMF lipids (% from total SM, PC, PE, PS, PI) |
|---|---|---|
| SM | 29.7 | 37.5 |
| PC | 27.9 | 28 |
| PE | 19.6 | 19.5 |
| PS | 13.3 | 9 |
| PI | 9.5 | 6 |
| Total | 100 | 100 |

The glycerophospholipids composition of the lipid preparation of the invention is also comparable and mimetic to HMF glycerophospholipids, as can be seen in the example presented in Table 4.

TABLE 4

| Lipid class | Lipid preparation of invention (% from total PC, PE, PS, PI) | Human Milk Fat (% from total PC, PE, PS, PI) |
|---|---|---|
| PC | 39.7 | 45.4 |
| PE | 27.8 | 30.8 |
| PS | 18.9 | 14.1 |
| PI | 13.5 | 9.7 |
| Total | 100 | 100 |

The composition of a specific lipid preparation of the invention is described in Table 5. As can be seen, the preparation consists mainly of high levels of HMF-like polar lipids, in contrast to the low levels of polar lipids found in the starting mixture. Thus, the preparation of the invention achieves levels of polar lipids which are equivalent to the levels found in HMF. These high levels permit the use of the preparations of the invention in a variety of infant nutritional articles, dietary supplements, functional foods, and pharmaceutical compositions.

It is important to note that the preparation of the invention is man-made, and its constituents, even when derived from natural sources, undergo processing/structuring before use in the preparation of the invention. Alternatively, these constituents are chemically or enzymatically synthesized. Therefore, the constituents that are comprised in the preparation of the invention contain at least traces of substances which are endogenous to the lipid sources from which they are derived (such traces being edible and physiologically compatible). Traces of this kind are absent from human milk (and from HMF), which makes the preparation of the invention similar, but not identical, to HMF.

In addition, HMF is the nomenclature used for the full lipid fraction of human milk. It definitely contains the constituents (the phospholipids) specifically mentioned herein, while also containing other lipid constituents which are not present in the lipid preparation of the invention, such as e.g. fat-soluble vitamins. Thus, the most preferred embodiment of the lipid preparation of the present invention comprises a combination of phospholipids whose ratio is comparable to that of HMF (SM>PC>PE>PS>PI or SM=PC>PE>PS>PI), and further comprises traces of substances from lipid sources from which said phospholipids are derived, while lacking other lipid constituents which are present in HMF.

TABLE 5

| Lipid class | Lipid preparation of invention (% w/w) |
|---|---|
| SM | 22.7 |
| PC | 21.4 |
| PE | 15.0 |
| PS | 10.2 |
| PI | 7.3 |
| Total | 76.6 |

The lipid preparation of the invention can be further manipulated, in order to become even more similar to HMF, by increasing the level of SM relative to the level of the glycerophospholipids. This can be achieved by using one of the following methods:

1. Taking advantage of the known stability of SM to alkaline hydrolysis, the lipid preparation of, for example, Table 5, is subjected to alkaline aqueous conditions. The glycerophospholipids undergo hydrolysis, resulting in the cleavage of their fatty acids and the production of free fatty acids and partially or fully hydrolyzed glycerophospholipids which are highly water soluble. Thus, the non-hydrolyzed, relatively hydrophobic SM can be easily separated and obtained by extraction to an organic or fatty media. The obtained SM can be further combined with the preparation of Table 5 (or other preparation of the invention), to obtain a lipid preparation in which the relative level of SM is higher and closer to that of HMF (around 38% of total polar lipids). Optionally, the alkaline hydrolysis is conducted partially, hydrolyzing only part of the glycerophospholipids. Thus, the hydrolysis process can be controlled in a way that the non-hydrolyzed glycerophospholipids and SM yield a lipid preparation which resembles the polar lipids of HMF even more closely that of the preparation of Table 5;

2. Utilizing selective enzymatic hydrolysis of glycerophospholipids, by applying a glycerophospholipid selective lipase to the polar lipid mixture of the invention (the preparation of table 5 for example). By using one or more of the following enzymes: 1:3 lipase, phospholipase A1 (PLA1) or phospholipase A2 (PLA2), the glycerophospholipids undergo hydrolysis of one or two of the fatty acids. The partially or fully hydrolyzed fatty acids can be separated from the SM as described following alkaline treatment. The obtained SM can be further combined with the preparation of Table 5 (or similar preparation). Alternatively, the selective enzymatic hydrolysis can be conducted partially, by applying less enzyme and/or having a shorter reaction time. This way, the remaining glycerophospholipids and SM yield a lipid preparation which resembles the polar lipids of HMF even more closely than the original preparation;

3. Using the different polarities between the different components of the preparation of the invention (SM>PC>PS>PI>PE) and conducting purification by means of normal phase preparative chromatography. The obtained SM can be further combined with the preparation of Table 5 (or similar preparation), to obtain a lipid preparation in which the relative level of SM is higher and closer to that of HMF;

4. Conducting a polar lipid extraction from the raw material (composed of proteins/sugars/lipids) through a selective solvent system that increases the content of SM in either the extract or the fraction of fat left and not extracted from raw material. Examples of extraction solvents are any alcohol or a combination of an alcohol and water. In this way, the SM, as the most polar component, is enriched relative to its concentration in the raw material. As previously described, the obtained SM may be combined with the original preparation (of table 5 for example) in order to obtain a lipid preparation richer in SM and more similar to HMF.

Thus, the present invention provides a lipid preparation which is obtained without mixing several lipid sources, but rather by the fractionation and treatment of natural polar lipids preparations, containing glycerophospholipids, preferably PC, PE, PS, and PI, and optionally comprising sphingomyelin (or precursors and/or metabolites of sphingomyelin). In accordance with the present invention, the polar lipids mixtures are obtained from raw lipid preparations extracted from natural sources, preferably marine source, more preferably animal source, and even more preferably bovine milk or poultry eggs. Milk of other mammals or eggs of other domesticated or wild birds are also suitable as a source. Furthermore, vegetal sources can be used whenever they contain glycerophospholipids at a relative ratio that permits their use without further mixing with other lipid sources, and/or the lipids of vegetal sources include PS and/or sphingomyelin (or precursors or metabolites of sphingomyelin). Examples or vegetal sources are soybeans, sweet potatoes and peanuts.

In preferred embodiments, the lipid preparation in accordance with the invention comprises above 1% w/w of each of PC, PE, PS and PI, and optionally above 1% w/w of sphingomyelin, preferably above 3% w/w of each of PC, PE, PS and PI, and optionally above 3% w/w of sphingomyelin, more preferably above 5% w/w of each of PC, PE, PS and PI, and optionally above 5% w/w of sphingomyelin, most preferably above 7% w/w of each of PC, PE, PS and PI, and optionally above 7% w/w of sphingomyelin.

In a further preferred embodiment the level of PC is above 5% w/w, more preferably above 10% w/w, most preferably above 15% w/w. The level of PC is preferably about 5-50% w/w, more preferably about 8-40% w/w, most preferably 10-35% w/w.

In a preferred embodiment the level of PS is above 2% w/w, more preferably above 4% w/w, most preferably above 7% w/w. The level of PS is preferably about 2-50% w/w, more preferably about 4-40% w/w, most preferably about 5-25% w/w.

In a preferred embodiment the level of PE is above 4% w/w, more preferably above 7% w/w, most preferably above 10% w/w. The level of PE is preferably about 3-50% w/w, more preferably about 5-40% w/w, most preferably about 7-30% w/w.

In a preferred embodiment the level of PI is about 2-50% w/w, more preferably about 3-40% w/w, most preferably about 4-20% w/w.

In a preferred embodiment the level of SM is above 3% w/w, more preferably above 5% w/w, more preferably above 10% w/w, most preferably above 15% w/w. The level of SM is preferably about 5-50% w/w, more preferably about 10-40% w/w, most preferably about 15-35% w/w.

In a specifically preferred embodiment the relative levels of the polar lipids (SM, PC, PE, PS, PI) mimic the relative levels of these lipids in HMF in which SM>PC>PE>PS>PI. Alternatively, said relative levels are SM=PC>PE>PS>PI. In more preferred embodiments the relative level of SM of total polar lipids (SM, PC, PE, PS, PI) is between 5-60%, more preferably 10-50%, even more preferably 20-40%, most preferably 30-35%.

In other specifically preferred embodiments the relative level of PC of total polar lipids (SM, PC, PE, PS, PI) is between 5-60%, more preferably 10-50%, more preferably 20-40%, even most preferably 25-35%.

In other specifically preferred embodiments the relative level of PE of total polar lipids (SM, PC, PE, PS, PI) is between 5-50%, more preferably 10-40%, most preferably 23-30%.

In other preferred embodiments the relative level of PS of total polar lipids (SM, PC, PE, PS, PI) is between 3-40%, more preferably 5-35%, even more preferably 7-25%, most preferably 10-20%.

In other preferred embodiments the relative level of PI of total polar lipids (SM, PC, PE, PS, PI) is between 2-40%, more preferably 3-35%, most preferably 5-20%.

In another preferred embodiment the relative levels of the glycero-polar lipids (PC, PE, PS, PI) mimic the relative levels of these lipids in HMF in which PC>PE>PS>PI. In a more preferred embodiments the relative level of PC out of total glycero-polar lipids (PC, PE, PS, PI) is between 5-60%, more preferably 10-55%, even more preferably 20-50%, most preferably 35-45%.

In another preferred embodiments the relative level of PE out of total glycero-polar lipids (PC, PE, PS, PI) is between 5-60%, more preferably 10-50%, even more preferably 15-45%, most preferably 20-35%.

In another preferred embodiment the relative level of PS out of total glycero-polar lipids (PC, PE, PS, PI) is between 3-50%, more preferably 5-45%, even more preferably 7-35%, most preferably 15-25%.

In yet another preferred embodiment the relative level of PI out of total glycero-polar lipids (PC, PE, PS, PI) is between 3-50%, more preferably 5-40%, most preferably 7-30%.

The preparation of the invention comprises high levels of PS, preferably above 2% w/w, preferably above 5% w/w, more preferably above 8% w/w, most preferably above 10% w/w. The said PS is of natural non-brain sources, preferably from milk or eggs, preferably bovine milk or poultry eggs. It is to be noted that the present invention can utilize a natural source of PS, comparable to soybean transphosphatidylated PS, but from a safe natural source. The preparation of the invention can serve as a good source of PS obtainable by extraction and not by transphosphatidylation. This PS can be used for the same purposes as commercial soybean transphosphatidylated PS, particularly as a dietary supplement or in functional foods or pharmaceutical preparations, for obtaining the health benefits associated with PS supplementation.

The preparation of the invention is also characterized by comprising high levels of SM, preferably above 3% w/w, more preferably above 5% w/w more preferably above 10% w/w, and most preferably above 15% w/w. The SM is of natural non-brain sources, preferably from milk or eggs, more preferably bovine milk or poultry eggs. Importantly, the preparation of the invention serves as an affordable source of SM, which is not from animal brain, and in the form, cost and grades applicable to dietary supplements, functional foods and/or pharmaceutical compositions, having brain-related health benefits.

Still further, the invention relates to a combination of PS and SM, for use in the treatment of brain related illnesses or disorders or for improving cognitive functions (mood deterioration, depression, stress, age-related disorders and diseases such as dementia, Alzheimer's disease, memory loss, problems of concentration and attention, learning capabilities, etc.).

The invention further relates to lipid preparations comprising PS and SM, optionally together with other polar lipids, which exhibit a synergistic beneficiary effect between the PS and SM. Both PS and SM are structural components of different tissues or parts of the human brain. PS is an important building block of cell membranes of grey matter and of nerve cells while SM is essential component of myelin sheaths. Thus the supplementation of these two important lipid-based brain building blocks has an increased positive effect on cognitive functions, by treating and maintaining the structural integrity of two brain systems simultaneously, in a synergistic, not merely additive manner. These compositions of PS and SM may contain above 1%, preferably 5-90% w/w, more preferably 5-60% w/w, most preferably 5-40% w/w of each of the PS and SM.

The invention specifically relates to a process of preparing the lipid preparation of the invention. This process comprises the steps of providing a suitable raw lipid source, removing from the raw lipid source non-lipid material by selectively dissolving the lipids in appropriate organic solvent or mixture of organic solvents.

The raw lipid source can be a mixture of different lipid sources, for example bovine milk combined with egg lecithin. Alternatively, each of the different sources may be treated independently by the process of the invention, and the final lipid mixtures obtained can be mixed to give a lipid preparation comprising polar lipids from varied sources.

In a preferred embodiment the lipid source is dispersed in a mixture of non-polar and a polar organic solvent/s or polar solvent alone. Preferred polar organic solvents are alcohols, preferably primary alcohols, more preferably ethanol, and preferred non-polar solvents are hydrocarbons, most preferably hexane. The solvent or solvent system optionally includes water, or alternatively the treatment with the organic solvents is preceded or followed by a treatment with an aqueous medium. The above mentioned treatments include dispersing the source of lipids in said media using agitation. The treatment is carried out at room temperature, or alternatively under cooling or heating conditions. Preferably the treatment, removal of non-lipid material, is carried out at temperatures where this removal is optimal and minimal amounts of lipids are removed. Preferably the process occurs at elevated temperatures, preferably 15-100° C., more preferably 25-80° C., most preferably 30-60° C. The non-lipid material is filtered off and is optionally further treated with said solvent systems to ensure minimal amounts of polar lipids are removed.

The organic solvents containing the lipids are removed by conventional methods, preferably by evaporation under reduced pressure. The lipid fraction is further de-oiled (removal of non-polar lipids, mainly triglycerides) by conventional methods, preferably, acetone or supercritical $CO_2$. In case of acetone, for example, the de-oiling step is repeated several times and the resulting polar lipids are filtered and dried by conventional methods, preferably under reduced pressure.

The preparation of the invention is suitable as a supplement or additive for infant formulas, as a source of HMF-like polar lipids, making said infant formulas more similar to human breast milk, as well as in baby or toddler's foods, enriching their nutritional content with HMF-like polar lipids.

The term "infant formula" as used herein encompasses infant formulas (for newborn to 6 months old infants), follow-up formulas (for 6-12 months old babies) and growing-up formulas (for 1-3 years old children).

The term "infant formula" as used herein encompasses infant formulas (for newborn to 6 months old infants), follow-up formulas (for 6-12 months old babies) and growing-up formulas (for 1-3 years old children).

The preparation of the invention can be further used to mimic or create fat globules which mimic human milk fat globules.

The preparation of the invention is also suitable in supplementing the nutrition of pregnant women, either as a dietary supplement, as an additive in functional foods, or as a pharmaceutical preparation.

The preparation of the invention can be used for the nutrition of pre-term infants as an additive in their nutrition, or as a pharmaceutical preparation.

The preparation of the invention can be further used as an active ingredient in dietary supplements, functional foods or pharmaceutical preparations for improving the health of all human beings, children, juveniles and young adults, adults, and especially the elderly.

A specific aspect of the present invention is the use of the preparation of the invention in improving the brain functions of any of the above populations, specifically by improving their cognitive functions, memory, alleviating stress, improving mood, improving age-associated memory deterioration, fighting dementia, preventing or treating Alzheimer's disease, etc.

The preparation of the invention may also be used for treating, preventing or improving myelin-related disorders or diseases, particularly de-myelination related disorders, such as for example MS, upon its administration (or consumption) to subjects in need.

The preparation of the invention is suitable for enabling normal brain and cognitive development of infants, toddlers and young children, through ensuring the normal or improved development of the myelin sheath and other sphingomyelin-related tissues.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

Lastly, the present invention also provides methods of treatment and/or improvement of cognitive functions, or brain-related illnesses or disorders, for a subject in need, said method comprising administering a therapeutically effective amount of the lipid preparations provided in the present invention to said subject. Said cognitive functions are memory, concentration, attention and learning capabilities. Said disorders are mood-, memory-, stress- or age-related neurological disorders, and diseases such as dementia, Alzheimer's disease, memory loss, problems of concentration and attention and learning capabilities.

In addition, wherein said method of treatment utilizes the lipid preparations of the invention comprising SM, said method is suitable for subjects suffering from myelin-related disorders or diseases, particularly de-myelination related disorders, such as multiple sclerosis (MS) and leukodystrophies.

Usually, a "therapeutically effective amount" is determined by the severity of the disease in conjunction with the preventive or therapeutic objectives, the route of administration and the patient's general condition (age, sex, weight and other considerations known to the attending physician). The decision as to the particular dosage to be employed (and the number of times to be administered per day) is within the discretion of the physician, and may be varied by titration of the dosage to the particular circumstances of this invention to produce the desired therapeutic effect.

The present invention further provides the use of the lipid preparations described in the invention in the preparation of pharmaceutical compositions for use in the treatment of the above-described conditions.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1—Preparation of a SM-Containing Polar Lipid Mixture 50 gr of bovine milk preparation (Table 2) were added to 400 ml of hexane:ethanol (80:20) and mixed together at 40-45° C. After 2 hrs, the slurry was vacuum filtered and the cake re-slurried under similar conditions and filtered again. The combined solvent fractions were evaporated under reduced pressure (<10 mbar). The lipid fraction obtained was further de-oiled twice with acetone in a ration of 1:6 (w/volume) and the powder obtained as sediments was filtered and dried under reduced pressure (<10 mbar) in a vacuum dryer. 7 gr of dry powder were obtained and analyzed to give the polar lipids distribution of Table 3 above.

The invention claimed is:

1. A man-made lipid preparation consisting of a mixture of the following natural, extracted, polar, bovine milk glycerophospholipids: bovine phosphatidylcholines (PC), bovine phosphatidylethanolamines (PE), bovine phosphatidylserines (PS), bovine phosphatidyl-inositols (PI), and bovine sphingomyelins (SM), wherein in the mixture the relative ratio by weight is SM>PC>PE>PS>PI and the percent by weight is:

SM, at least 10% w/w;
PC, at least 7% w/w/;
PE, at least 4% w/w;
PS, at least 2% w/w; and
PI, at least 1% w/w.

* * * * *